United States Patent [19]

Young

[11] Patent Number: 4,461,730

[45] Date of Patent: * Jul. 24, 1984

[54] METHOD FOR THE SELECTIVE PREPARATION OF SECONDARY ALCOHOLS AND DERIVATIVES THEREOF

[75] Inventor: Lewis B. Young, Skillman, N.J.

[73] Assignee: Mobil Oil Corporation, New York, N.Y.

[*] Notice: The portion of the term of this patent subsequent to Dec. 21, 1999 has been disclaimed.

[21] Appl. No.: 410,286

[22] Filed: Aug. 23, 1982

Related U.S. Application Data

[63] Continuation-in-part of Ser. No. 222,850, Jan. 6, 1981, abandoned.

[51] Int. Cl.³ ............... C07C 67/04; C07C 27/02; C07C 41/03
[52] U.S. Cl. ............... 260/459 R; 568/877; 568/618; 560/247; 260/980; 564/296; 252/351; 252/353; 252/357; 252/DIG. 1
[58] Field of Search ............... 560/247; 568/858, 877, 568/618; 260/459 R, 980; 564/296

[56] References Cited

U.S. PATENT DOCUMENTS

| | | | |
|---|---|---|---|
| 1,970,578 | 8/1934 | Schoeller et al. | 568/622 X |
| 2,671,116 | 3/1954 | Kosmin | 568/622 |
| 3,492,341 | 1/1970 | Trevillyan | 560/247 |
| 4,251,673 | 2/1981 | Mark et al. | 568/858 |
| 4,365,083 | 12/1982 | Young | 560/247 |
| 4,365,084 | 12/1982 | Young | 560/247 |

OTHER PUBLICATIONS

Morrison et al., Organic Chemistry, 3rd Ed., (1973), 455 & 752.
Schick, Nonionic Surfactants, (1967), 384.
Brewster, Organic Chemistry, (1948), 228-229.
Kirk–Othmer Encyclopedia of Chemical Technology, Third Edition, vol. 1, pp. 728-729, (1978), Regarding the Conversion of Alcohols to Surfactants.

Primary Examiner—Bernard Helfin
Attorney, Agent, or Firm—A. J. McKillop; M. G. Gilman; E. F. Kenehan, Jr.

[57] ABSTRACT

A method for the preparation of secondary alcohol mixtures by selective reaction of an olefin or olefin mixture and a carboxylic acid compound in the presence of zeolite mordenite. The reaction selectively produces α-methylalkyl carboxylate enriched ester product which, upon subsequent hydrolysis, yields the desired secondary alcohol product enriched in alcohols having hydroxy functionality at the 2-position.

13 Claims, No Drawings hydroxy alkyl compound with very little, if any, 3-hydroxy or higher structural isomer byproduct therein.

The particular zeolite material employed to promote the novel, selective addition reaction step of this invention is the zeolite mordenite. Mordenite may be synthetically prepared or naturally occurring. Dealuminized mordenites, i.e., those subjected to acid treatment to increase the silica to alumina mole ratio to a relatively high level, are preferred.

In a preferred embodiment of the present invention, olefin mixtures are employed as the olefinic reactant in the first step of the process. Such mixture contains at least 25 mole percent of a $C_6$–$C_{20}$ olefin having no unsaturation at the site of the No. 2 carbon atom of the olefin.

DESCRIPTION OF SPECIFIC EMBODMENTS

The subject of the present invention is a process for the manufacture of secondary alcohol mixtures having a high degree of hydroxy functionality at the 2-position of the hydrocarbon chain. Such mixtures are those which are enriched in alcohols represented by the formula:

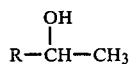

wherein R is alkyl of 1 to 18 carbon atoms. These types of alcohol mixtures, and surfactant chemicals based thereon, are found to have superior biodegradability as compared to similar compounds having random functional group points of attachment.

The first, and key, step in the process is the reaction of an olefin with a carboxylic acid compound to selectively produce an alkyl carboxylate ester product enriched in the α-methylalkyl carboxylate ester. The reaction is carried out under ester-forming conditions which include temperatures of between 25° C. and 600° C. and pressures within the approximate range of $10^4$ Pa to $10^7$ Pa (0.1–100 atm), although temperatures of 75° C. to 400° C. and pressures between $10^5$ Pa and $4 \times 10^6$ Pa are preferred. By utilization of the particular type of zeolite catalyst described hereinafter, it now becomes possible to react carboxylic acids with olefinic hydrocarbons having the carbon-carbon double bond in substantially any position in the molecule and to selectively produce an adduct wherein the carboxylate has attached principally at the #2 carbon of the olefin molecule.

The carboxylic acids useful in the process of the present invention are preferably alkyl carboxylic acids having from 1 to about 10 carbon atoms therein. Included within this group are formic acid, acetic acid, propionic acid, butyric acid and hexanoic acid. Slightly branched alkyl carboxylic acids are also useful, such as, for instance, isobutyric acid. Haloalkyl carboxylic acids, such as chloroacetic acid, fluoroacetic acid and trifluoroacetic acid may be employed. Also, aryl carboxylic acids will be found desirable in some instances, including benzoic acid, para-toluic acid and para-chlorobenzoic acid. For commercially viable applications, it is expected that acetic acid will be found particularly desirable.

Olefins suitable for the selective production of α-methylalkyl carboxylate enriched mixtures as described herein are not limited to α-olefins. Rather, it has been found that substantially any olefinic hydrocarbon may be employed without regard to the location of the site of unsaturation. Mixed isomers of a given olefin are particularly desirable due to their ready availability and relatively low cost. Linear $C_3$ to $C_{20}$ olefins are especially preferred, but slightly branched olefins may also be employed. Some non-limiting illustrative examples would include: 1- and 2-pentenes, 1-, 2-, 3- and 4-octenes (or mixtures thereof), dodecenes, hexadecenes, 1-methylnonenes, 4-phenyl-1-butene, and so forth. Especially preferred olefinic reactants are olefin mixtures containing at least 25% of a $C_6$ to $C_{20}$ olefin having no unsaturation at the site of the No. 2 carbon atoms thereof. It is especially surprising that internal olefins of this type can comprise a substantial part or even all of the olefinic reactant and still have the resulting alkyl carboxylate product enriched in the α-methylalkyl carboxylate.

The zeolite material utilized as the catalyst to promote the ester-forming first step in the process of this invention is known as mordenite. This zeolite is naturally occurring and, in its natural state, normally has a silica to alumina mole ratio approximately equal to 5–10. However, a large part of the alumina can be removed from the mordenite crystal framework, thereby substantially increasing the silica to alumina mole ratio, by acid extraction or "leaching". This increases the effective pore diameter and thus diffusivity of reactant and product molecules to and from the active sites. Acid extraction, commonly referred to as de-aluminization of the zeolite, is generally accomplished by treatment with strong mineral acids which, in addition to removing $Al_2O_3$, also replace metal cations (e.g. $Na^+$) with hydrogen ions. In the process of the herein disclosed invention, the utilization of de-aluminized mordenites is preferred.

Mordenite can also be prepared synthetically. One method of synthesis is disclosed by L. B. Sand in U.S. Pat. No. 3,436,174. Another will be found in U.S. Pat. No. 3,574,539, issued to D. Domine and J. Quobex. Both patents are incorporated herein by reference for the purpose of showing synthetic methods of mordenite preparation.

In practicing the ester-forming step of the process, it may be useful to incorporate the above-described crystalline zeolite in another material resistant to the temperature and other conditions employed in the process. Such matrix materials include synthetic or naturally occurring substances as well inorganic materials such as clay, silica, and/or metal oxides. The latter may be either naturally occurring or in the form of gels or gelatinous precipitates including mixtures of silica and metal oxides. Naturally occurring clays which can be composited with the zeolite include those of the montmorillonite and kaolin families, which families include the sub-bentonites and the kaolins commonly known as Dixie, McNamee-Georgia and Florida clays or others in which the main mineral constituent is halloysite, kaolinite, dickite, nacrite or anauxite. Such clays can be used in the raw state as originally mined or initially subjected to calcination, acid treatment, or chemical modification.

In addition to the foregoing materials, the zeolites employed herein may be compounded with a porous matrix material, such as alumina, silica-alumina, silica-magnesia, silica-zironia, silica-thoria, silica-beryllia, and silica-titania, as well as ternary combinations, such as silica-alumina-thoria, silica-alumina-zirconia, silica-alumina-magnesia and silica-magnesia-zirconia. The matrix may be in the form of a cogel. The relative proportions of finely divided zeolite and inorganic oxide gel matrix may vary widely, with the zeolite content

METHOD FOR THE SELECTIVE PREPARATION OF SECONDARY ALCOHOLS AND DERIVATIVES THEREOF

CROSS REFERENCE TO RELATED APPLICATION

This application is a continuation-in-part of the copending application of Lewis B. Young, said application having Ser. No. 222,850, filed Jan 6, 1981 now abandoned.

BACKGROUND OF THE INVENTION

1. Field of the Invention

The invention disclosed herein is concerned with the preparation of secondary alcohol mixtures which are enriched in $C_3$–$C_{20}$ alkanols having hydroxy functionality in the 2-position. Such mixtures are prepared from olefinic compounds in the presence of carboxylic acids and particular zeolite catalysts.

2. Description of the Prior Art

Secondary alcohols can be prepared by hydrolysis of secondary alkyl carboxylate esters. The production of such alcohol precursors by reaction of carboxylic acids with olefins in the presence of Lewis Acid catalysts is known. However, the reaction results in the apparently indiscriminate addition of the carboxylate to either end of the olefin double bond, thereby giving rise to a mixture of structural isomers of the alkylcarboxylate product. Mineral acids (e.g. $H_2SO_4$) are also reported to catalyze the reaction, but the result is much the same, i.e. non-selective addition of the carboxylic acid to either side of the carbon-carbon double bond. Trevillyan; U.S. Pat. No. 3,492,341; Issued Jan. 27, 1970 discloses preparation of alkyl carboxylate esters by reacting carboxylic acids with 1- or 2-monoolefins over a mordenite zeolite catalyst.

Prior to the present invention the only known method for producing commercially valuable secondary alcohol mixtures enriched in alcohols having the hydroxy group in the 2-position has been to utilize substantially pure, but expensive, alpha-olefins as the starting material. Reaction of carboxylic acids with internal or mixed olefins using the common acid catalysts necessitated physical separation of the isomeric and structural variants of the alkyl carboxylic product (e.g. by distillation) in order to isolate the desired α-methylalkyl carboxylate alcohol precursor. Subsequent hydrolysis of the α-methylalkyl carboxylates in the product resulted in almost stoichiometric conversion to the 2-alcohol.

The resulting secondary alcohols can be converted into nonionic detergents by reaction with ethylene oxide. It has been shown that detergents of this type which contain a high degree of hydroxy functionality in the 2-position, are superior in biodegradability to comparable ethoxylates having random hydroxy functional attachment up and down the carbon chain.

Detergent range higher alcohols and their derivatives are used in a wide variety of industrial and consumer products. In general, these materials are used either for their surface-active properties, or as a means of introducing a long chain moiety into a chemical compound. Only a small amount of detergent range alcohol is used as is, but rather most of it is used as derivative such as poly(oxyalkylene) ethers, or esters of acids such as sulfuric acid, phosphoric acid, and mono- and dicarboxylic acids.

Surfactants derived from detergent range alcohols are widely used where emulsifying, dispersing, wetting, or detergent properties are desired. These surfactants are readily biodegradable and are finding increased use in low phosphate and nonphosphate detergents. The alcohols provide the starting material for all of the surfactant types: nonionics, anionics, cationics and zwitterionics. The alkyl sulfates, such as sodium dodecyl sulfate, $C_{12}H_{25}OSO_3Na$, are known for their cleaning ability and voluminous, stable foam. Alkyl sulfates derived from $C_{12}$ through $C_{15}$ linear alcohols are widely used in consumer products, for instance in toothpastes, hair shampoos, carpet shampoos, and light-duty household cleaners, whereas those derived from $C_{16}$ and $C_{18}$ linear alcohols are used in heavy-duty household detergents. Detergents having good foam stability have been reported from mixtures of $C_{14}$, $C_{16}$, and $C_{18}$ linear alcohols. Minor amounts of unsulfated alcohol left in the alkyl sulfate detergents serve as foam stabilizers. The polyethoxylated alcohols, when sulfated and neutralized with a base such as sodium or ammonium hydroxide to give anionic surfactants, have wide application as light-duty dishwashing detergents and as part of the surfactant system of heavy-duty household liquid and granular detergents. These and other more specialized surfactants have a wide variety of industrial and household applications.

Cationic quaternary nitrogen surfactants of various types may be made by the condensation of tertiary amines with long chain alkyl halides, which are in turn obtained from the halogenation of a higher alcohol. Besides their use as surfactants, quaternary derivatives are widely used as disinfectants, bactericides, fungicides, antistatic agents, and textile softeners. Specialty phosphate ester surfactants and emulsifying agents are made by the reaction of phosphorous pentoxide and a detergent range alcohol. Other surfactants derived from these alcohols are alkyl amine oxides and alkyl glyceryl sulfonates.

In another example of a surfactant application, dodecanol is used as a stabilizer for fire extinguishing foams. Hexadecanol and octadecanol are used in bar soaps and as antifoam agents in paper making and wastewater treatment, and dodecanol or higher alcohols are used to limit foaming in detergent compositions. The emulsion polymerization of various monomers is practiced in the presence of an alkyl sulfate surfactant, sometimes combined with free alcohol.

SUMMARY OF THE INVENTION

A method has now been found whereby substantially any linear olefinic compound, especially including mixtures of olefinic compounds, regardless of the position of the carbon-carbon double bond in the hydrocarbon chain, may be converted to secondary alcohol mixtures enriched in alcohols having hydroxy functionality in the 2-position. The conversion is accomplished by reaction under ester-forming conditions of the olefin or olefin mixtures with a $C_1$ to $C_{10}$ carboxylic acid compound, in the presence of a particular type of shape-selective zeolite catalyst, to selectively produce an alkyl carboxylate ester product enriched in α-methylalkyl carboxylate. The carboxylate ester product can then be hydrolyzed under hydrolysis conditions to yield the corresponding alcohol mixture enriched in the 2-

TABLE I

| Reaction Of 1-Decene And Acetic Acid | | | |
|---|---|---|---|
| Temperature | 120° C. | 120° C. | 120° C. |
| Reaction Time, hrs. | 1 | 25 | 47 |
| C$_{10}$ Product Distribution | | | |
| C$_{10}$H$_{20}$ | 65 wt % | 29 wt % | 29 wt % |
| C$_{10}$H$_{21}$OAC | 26 wt % | 58 wt % | 58 wt % |
| (C$_{10}$H$_{20}$)$_2$ | 9 wt % | 13 wt % | 13 wt % |
| C$_{10}$H$_{21}$OAc Isomer Distribution | | | |
| 2- | | 80% | 75% |
| 3- | | 19% | 23% |
| 4- | | 0.9% | 1.3% |
| 5- | | 0.2% | 0.3% |

EXAMPLE 2

Using another sample of the same mordenite catalyst, 1-octene and acetic acid (mole ratio=1:4) were reacted in the manner described in Example 1. The results of the analysis are shown in TABLE II. Again, it is seen that the 2-isomer (2-octylacetate) is selectively produced relative to the higher isomers.

TABLE II

| Reaction Of 1-Octene And Acetic Acid | | | |
|---|---|---|---|
| Temperature | 120° C. | 120° C. | 120° C. |
| Reaction Time, hrs. | 2.5 | 5 | 23 |
| C$_8$ Product Distribution | | | |
| C$_8$H$_{16}$ | 61.6 wt % | 47.9 wt % | 36.6 wt % |
| C$_8$H$_{17}$OAc | 31.7 wt % | 45.5 wt % | 57.8 wt % |
| (C$_8$H$_{16}$)$_2$ | 6.7 wt % | 6.6 wt % | 5.6 wt % |
| C$_8$H$_{17}$OAc Isomer Distribution | | | |
| 2- | 93.6% | 91.6% | 85.4% |
| 3- | 6.4% | 8.4% | 14.0% |
| 4- | — | — | 0.6% |

EXAMPLE 3

2-Octene and acetic acid (mole ratio=1:2) were reacted in the presence of the mordenite catalyst as described above. The results are summarized in TABLE III.

EXAMPLE 4 (COMPARATIVE)

A mixture of 2-octene and acetic acid (mole ratio=1:4) were reacted in the presence of a conventional Lewis Acid catalyst (boron trifluoride etherate). The reaction was carried out on a steam bath at 90° C. and samples were removed and analyzed at 1.2 and 2.7 hours. The results are given in TABLE III.

TABLE III

| Reaction Of 2-Octene And Acetic Acid | | | | | |
|---|---|---|---|---|---|
| Catalyst | Mordenite | | | BF$_3$ | Et$_2$O |
| Temperature | 120° C. | 120° C. | 120° C. | 90° C. | 90° C. |
| Reaction Time, hrs. | 0.5 | 18 | 43 | 1.2 | 2.7 |
| Yield of C$_8$OAc, wt % | 19 | 60 | 59 | 37 | 57 |
| C$_8$H$_{17}$OAc Isomer Distribution | | | | | |
| 2- | 64% | 64% | 63% | 52% | 52% |
| 3- | 36% | 34% | 34% | 45% | 44% |
| 4- | — | 2% | 3% | 3% | 4% |

A significant improvement in selectivity to the 2-isomer is seen for the reaction over the mordenite catalyst vis-à-vis the convention BF$_3$Et$_2$O carboxylation catalyst.

EXAMPLE 5

A 1:2 molar ratio mixture of 4-octene and acetic acid was mixed with the mordenite catalyst of Example 1 and heated to reflux. Samples were taken at 4 and 22 hours and analyzed. The results are summarized in TABLE IV.

EXAMPLE 6 (COMPARATIVE)

For purposes of comparison, a mixture of 4-octene and acetic acid were heated on a steam bath to 90° C. in the presence of BF$_3$Et$_2$O. The results of this reaction are also shown in TABLE IV.

TABLE IV

| Reaction of 4-Octene and Acetic Acid | | | | |
|---|---|---|---|---|
| Catalyst | Mordenite | | BF$_3$ | Et$_2$O |
| Temperature | 120° C. | 120° C. | 90° C. | 90° C. |
| Reaction Time, hrs. | 4 | 22 | 0.6 | 4.3 |
| Yield of C$_8$OAc, wt % | 10 | 31 | 9 | 66 |
| C$_8$H$_{17}$OAc Isomer Distribution | | | | |
| 2- | 31% | 41% | 1% | 8% |
| 3- | 46% | 38% | 5% | 18% |
| 4- | 23% | 20% | 94% | 75% |

As will be seen from the data, the conventional Lewis Acid catalyst resulted in an alkyl carboxylate product which was almost entirely the 4-isomer, as would normally be expected due to the location of the carbon-carbon double bond. In contrast, the mordenite zeolite catalyst provided a product mixture having only minor amounts of the 4-isomer and a substantial increase in the proportion of the 2- and 3-isomers. The selectivity to the 2-isomer is especially surprising in view of the internal position of the unsaturated site.

When in the Example 5 procedure the 4-octene reactant is replaced by an octene mixture comprising 25% each of 1-octene, trans-2-octene, trans-3-octene, and trans-4-octene, substantial selectivity (i.e., at least 40% of alkyl carboxylate product) to production of the 2-C$_8$H$_{17}$OAc isomer results.

Subsequent hydrolysis of the α-methylalkyl-enriched carboxylate products of these examples by conventional hydrolysis techniques will be substantially quantitative. Further, the reaction causes very little, if any, isomerization of the alkylate so that the α-methylalkyl carboxylate is converted substantially in its entirety to the desired 2-alcohol.

Although the foregoing will illustrate certain preferred embodiments of the process of my invention, it is of course to be understood that numerous variations thereon may be made without departing from the spirit asnd scope of the invention. Such being the case, there should be no undue limitation implied except as expressly set forth by the following claims.

What is claimed is:

1. A process for the preparation of secondary alcohol mixtures enriched in alcohols of the formula

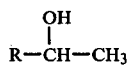

$$\begin{array}{c} \text{OH} \\ | \\ \text{R—CH—CH}_3 \end{array}$$

wherein R is alkyl of 1 to 18 carbon atoms, said process comprising
 (A) reacting an olefin mixture containing at least 25 percent of a C$_6$ to C$_{20}$ olefin having no unsaturation at the site of the No. 2 carbon atom thereof, with a ranging between from about 1 to about 99 percent by weight and more usually in the range of about 5 to about 80 percent by weight.

The carboxylate ester forming step of the process described herein may be carried out as a batch-type, semi-continuous or continuous operation utilizing a fixed or moving bed catalyst system. A preferred embodiment entails use of a catalyst zone wherein the hydrocarbon charge is passed concurrently or countercurrently through a moving bed of particle-form catalyst. The latter, after use, can be conducted to a regeneration zone where coke is burned from the catalyst in an oxygen-containing atmosphere (such as air) at elevated temperature, after which the regenerated catalyst is recycled to the conversion zone for further contact with the organic reactants.

As indicated, the alkyl carboxylate reaction product is enriched in the α-methylalkyl carboxylate isomer. For purposes of the present invention, the alkyl carboxylate product is enriched in α-methylalkyl carboxylate when the α-methylalkyl isomer comprises at least 40% of the total alkyl carboxylate product. Preferably the α-methylalkyl isomer comprises at least 50% or even at least 60% of the total alkyl carboxylate product.

The α-methylalkyl enriched carboxylate product of the first step of the process can then be hydrolyzed under hydrolysis conditions to convert the ester functionality to the corresponding secondary alcohol. The hydrolysis of esters is well known in the chemical literature and may be carried out in any of a number of ways.

In general, the reaction is normally carried out in basic medium wherein the ester is cleaved to produce the salt of the corresponding carboxylic acid and to hydrolyze the methylalkyl moiety to the alcohol, with the —OH function replacing the ester at the same point of attachment to the carbon chain. The reaction is straightforward and substantially quantitative, with no migration of the point of attachment, so that the α-methylalkyl-enriched carboxylate product is converted substantially entirely to the secondary alcohol. The salt of the carboxylic acid may be recovered and hydrolyzed back to the acid for subsequent recycling for further reaction with olefins as discussed hereinabove.

A preferred method of hydrolyzing the ester product contemplates refluxing with aqueous sodium or potassium hydroxide solution. The alkaline mixture is thereafter distilled to recover the alcohol. If necessary, the distillate may be saturated with sodium or potassium carbonate to liberate the alcohol—i.e., separate it from the aqueous component of the distillate.

The hydrolysis reaction may be carried out on the entire product mixture of the foregoing carboxylation reaction step or, alternatively, the α-methylalkyl-enriched carboxylate may be separated from some or all of the other components of the carboxylation reaction product mixture. In either event, the hydrolysis reaction product is subsequently separated by conventional means, such as fractional distillation, to recover an alcohol product fraction enriched in the desired secondary alcohol isomer having hydroxy functionality in the 2-position. As with the alkyl carboxylate product of the initial process step, the alcohol product is enriched in alcohols having hydroxy functionality at the 2-position for purposes of this invention if this 2-isomer comprises at least 40% of the total alcohol product. Again preferably the secondary alcohol having hydroxy functionality in the 2-position comprises at least 50% or even at least 60% of the total alcohol product.

In one embodiment of the invention, the secondary alcohols prepared as taught above are subsequently converted to a surfactant material having a high degree of functionality in the 2-position of the alkyl chain. Such surfactants are particularly desirable in applications wherein there is a likelihood that some or all of it may eventually find its way into the natural environment. While surfactants derived from detergent range alcohols are known to be generally biodegradable, it is also known that compounds exhibiting a high degree of 2-functionality are significantly superior to similar compounds having random functional group attachment in terms of biodegradability. The method of the present invention provides a relatively inexpensive way to obtain those very desirable 2-functional surfactants from a readily available mixed olefin starting material.

The surfactant derivatives of the secondary alcohols produced as provided above may be any of usual surfactant types: nonionic, anionic, cationic or zwitterionic. The techniques for preparing these types of surfactants are straight forward and well known to those conversant in the art. Generic teachings and/or discussions on the subject of preparing surfactant compounds from organic alcohols are to be found in the literature, such as, for example, the text entitled SURFACE ACTIVE AGENTS, THEIR CHEMISTRY AND TECHNOLOGY, Vol. 1, pp 202–205, by A. M. Schwartz and J. W. Perry (Interscience Publishers, Inc., 1949). Non-ionic detergents, for example, may be prepared by reaction of an alcohol with ethylene oxide or propylene oxide to introduce ether groups into the molecule to increase the hydrophilic character of the compound. The reaction is carried out under moderate conditions of temperature and pressure in the presence of alkaline catalysts. The number of ether groups necessary to effect complete water solubility depends, of course, on the molecular weight and structure of the hydrophobic portion of the molecule.

A particularly preferred embodiment of the invention contemplates conversion of the 2-alcohol enriched product, prepared as disclosed herein, to a nonionic detergent such as that derived from reaction of ethylene oxide with linear secondary alcohols.

Another embodiment contemplates the utilization of the 2-alcohol enriched product, prepared as described herein (e.g. 2-octanol), as a component of a phthalate plasticizer (i.e. dioctylphthalate) used to modify the properties of polymers.

The following examples are provided to illustrate the process of this invention, and particularly the critical first step thereof, to aid those in the art in the understanding and practice thereof.

EXAMPLE 1

A sample of a commercially available mordenite zeolite catalyst (Zeolon 500) was de-aluminized by extraction with 0.5N HCl to adjust the silica to alumina mole ratio to approximately 85. One-tenth of a gram of the dried, de-aluminized zeolite was ground to a powder and added to 10 ml of a mixture of 1-decene and acetic acid (mole ratio=1:4). The mixture was heated to reflux and samples were periodically removed and analyzed. As will be seen from the summary provided in TABLE I, the product of the reaction was overwhelmingly the 2-isomer (2-decylacetate) with minor amounts of the 3-, 4- and 5-isomers as byproducts.

$C_1$ to $C_{10}$ carboxylic acid, said reaction being carried out under ester-forming reaction conditions including the presence of a catalyst comprising the crystalline zeolite material mordenite, to thereby selectively produce an alkyl carboxylate ester product which is enriched in the α-methylalkyl craboxylate ester, and (B) subsequently hydrolyzing said α-methylalkyl carboxylate-enriched ester product under hydrolysis reaction conditions, to thereby provide said secondary alcohol mixture enriched in alcohols having hydroxy functionality at the 2-position.

2. The process of claim 1 wherein said ester-forming reaction conditions include a temperature of between about 25° C. and 600° C. and at a pressure of within the range of $10^4$ Pa to $10^7$ Pa.

3. The process of claim 2 wherein said carboxylic acid is selected from acetic acid, propionic acid and butyric acid.

4. The process of claim 1 wherein the olefins in said olefin mixture are linear or slightly branched and have from 3 to about 20 carbon atoms therein.

5. The process of claim 1, 2, 3 or 4 wherein said mordenite zeolite is dealuminized.

6. The process of claim 5 wherein said zeolite additionally comprises a binder therefor.

7. The process of claim 1 wherein said hydrolysis conditions include carrying out said hydrolysis reaction in a basic medium.

8. The process of claim 7 wherein said basic medium comprises an aqueous solution of sodium hydroxide or potassium hydroxide.

9. The process of claim 1 further comprising the step of converting said secondary alcohol mixture to a surface active agent, wherein said secondary alcohol mixture is converted to a nonionic detergent by reaction with ethylene oxide.

10. The process of claim 1 further comprising the step of converting said secondary alcohol mixture to a surface active agent, wherein said secondary alcohol mixture is sulfated.

11. The process of claim 1 further comprising the step of converting said secondary alcohol mixture to a surface active agent, wherein said secondary alcohol mixture is polyethoxylated, then sulfated and then neutralized with sodium hydroxide or ammonium hydroxide.

12. The process of claim 1 further comprising the step of converting said secondary alcohol mixture to a surface active agent, wherein said secondary alcohol mixture is halogenated and condensed with a tertiary amine to form a cationic quaternary nitrogen surfactant.

13. The process of claim 1 further comprising the step of converting said secondary alcohol mixture to a surface active agent, wherein said secondary alcohol mixture is reacted with phosphorus pentoxide to produce a phosphate ester surfactant.

* * * * *